US012691053B2

(12) United States Patent
Morikawa et al.

(10) Patent No.: US 12,691,053 B2
(45) Date of Patent: Jul. 28, 2026

(54) PHOTOCURABLE RESIN COMPOSITION FOR NAIL OR ARTIFICIAL NAIL, CURED PRODUCT, AND METHOD FOR COATING NAIL OR ARTIFICIAL NAIL

(71) Applicant: THREEBOND CO., LTD., Tokyo (JP)

(72) Inventors: Yumi Morikawa, Tokyo (JP); Takanori Wachi, Tokyo (JP)

(73) Assignee: THREEBOND CO., LTD., Tokyo (JP)

( * ) Notice: Subject to any disclaimer, the term of this patent is extended or adjusted under 35 U.S.C. 154(b) by 548 days.

(21) Appl. No.: 18/005,585

(22) PCT Filed: Jul. 5, 2021

(86) PCT No.: PCT/JP2021/025282
§ 371 (c)(1),
(2) Date: Jan. 13, 2023

(87) PCT Pub. No.: WO2022/019097
PCT Pub. Date: Jan. 27, 2022

(65) Prior Publication Data
US 2023/0270659 A1 Aug. 31, 2023

(30) Foreign Application Priority Data

Jul. 21, 2020 (JP) ................................. 2020-124433

(51) Int. Cl.
| | |
|---|---|
| *A61K 8/87* | (2006.01) |
| *A61K 8/81* | (2006.01) |
| *A61K 8/86* | (2006.01) |
| *A61Q 3/02* | (2006.01) |
| *C08F 290/06* | (2006.01) |
| *C09D 151/08* | (2006.01) |

(52) U.S. Cl.
CPC .............. *A61K 8/87* (2013.01); *A61K 8/8147* (2013.01); *A61K 8/86* (2013.01); *A61Q 3/02* (2013.01); *C08F 290/067* (2013.01); *C09D 151/08* (2013.01); *A61K 2800/95* (2013.01)

(58) Field of Classification Search
None
See application file for complete search history.

(56) References Cited

U.S. PATENT DOCUMENTS

| | | |
|---|---|---|
| 10,149,807 B1 | 12/2018 | Li et al. |
| 2010/0008876 A1 | 1/2010 | Tanaka et al. |
| 2016/0007713 A1 | 1/2016 | Gouse |
| 2017/0319461 A1 | 11/2017 | Chen et al. |
| 2019/0274407 A1 | 9/2019 | Ma |

FOREIGN PATENT DOCUMENTS

| | | |
|---|---|---|
| JP | 2010-037330 A | 2/2010 |
| JP | 2015-025935 A | 2/2015 |
| JP | 2015-209375 A | 11/2015 |
| JP | 2017-66136 A | 4/2017 |
| JP | 2017-203023 A | 11/2017 |
| JP | 2019-156827 A | 9/2019 |
| JP | 6656662 B1 | 3/2020 |
| JP | 2020-055772 A | 4/2020 |
| JP | 2020-093983 A | 6/2020 |
| WO | 2017057309 A1 | 4/2017 |

OTHER PUBLICATIONS

Rejection Decision ("Communication") dated Sep. 13, 2024, issued for the corresponding Chinese Patent Application No. 202180048421.X, 14 pages, with English translation.
Office Action, dated Jan. 22, 2025, which was issued for the corresponding Taiwanese Patent Application No. 110125200, 22 pages, with English translation.
Office Action, dated May 20, 2025 which was issued for the corresponding Japanese Patent Application No. 2022-538677, 11 pages, with English translation.
Office Action, dated May 16, 2025, which was issued for the corresponding Taiwanese Patent Application No. 110125200, 12 pages, with English translation.
State Intellectual Property Office of People's Republic of China, a First Notice of Examination Action dated Jan. 21, 2024, issued for related Chinese Patent Application No. 202180048421.X and its English translation (14 sheets).
State Intellectual Property Office of People's Republic of China, a Second Office Action dated Jul. 20, 2024, issued for related Chinese Patent Application No. 202180048421.X and its English translation (13 sheets).
European Patent Office, "Extended European Search Report" dated Jul. 19, 2024 in connection with the related European patent application No. 21846623.3, 9 pages.
International Search Report for the corresponding Patent Application No. PCT/JP2021/025282 dated Sep. 21, 2021, with English translation.
Office Action, dated Aug. 27, 2025, which was issued for the corresponding Vietnamese Patent Application No. 1-2023-00394, 4 pages, with English translation.

*Primary Examiner* — Nicole P Babson
(74) *Attorney, Agent, or Firm* — LUCAS & MERCANTI, LLP

(57) ABSTRACT

A photocurable resin composition for a nail or an artificial nail can form a cured product that has excellent transparency and gloss while having hardness required for coating a nail or an artificial nail. The photocurable resin composition for a nail or an artificial nail contains components (A) to (D): component (A): a urethane (meth)acrylate oligomer, component (B): a compound having three or more (meth) acryloyl functional groups (excluding the component (A)), component (C): a compound having a molecular weight of 200 or less and having a hydroxyl group and a methacryloyl group (excluding the components (A) and (B)), and component (D): a photoinitiator.

8 Claims, No Drawings

PHOTOCURABLE RESIN COMPOSITION FOR NAIL OR ARTIFICIAL NAIL, CURED PRODUCT, AND METHOD FOR COATING NAIL OR ARTIFICIAL NAIL

CROSS REFERENCE TO RELATED APPLICATION

This Application is a 371 of PCT/JP2021/025282 filed on Jul. 5, 2021 which, in turn, claimed the priority of Japanese Patent Application No. 2020-124433 filed on Jul. 21, 2020, both applications are incorporated herein by reference.

TECHNICAL FIELD

The present invention relates to a photocurable resin composition suitable for coating a nail, a cured product, and a method for coating a nail or an artificial nail.

BACKGROUND ART

Conventionally, a photocurable resin composition (UV nail gel) containing a photopolymerizable monomer and/or oligomer is known in the field of nail care. These UV nail gels are intended to decorate and make up a nail by being applied to the nail using a brush or the like and then irradiated with light to be cured, and a decorative nail film having beautiful gloss and high adhesion to the nail can be obtained. In nail decoration using this UV nail gel, a decorative nail film is generally formed of a multilayer including a base coat layer, a color layer, and a top coat layer. Among them, in the top coat layer, in order to make the decoration of the underlayer look beautiful, a colorless and transparent appearance is most important as well as its gloss, and the top coat layer also needs to be hard enough to coat the nail or the artificial nail while protecting the decoration.

According to the technique of JP 2010-37330 A (corresponding to US 2010/0008876 A), proposed as an artificial nail composition that hardly turns yellow and is excellent in internal curability is an artificial nail composition including a compound (component (a)) having a radical polymerizable unsaturated double bond; and a component (component (b)) selected from the group consisting of (i) an acylphosphine oxide-type photopolymerization initiator, and (ii) a mixture of an acylphosphine oxide-type photopolymerization initiator and an α-hydroxyalkylphenone-type photopolymerization initiator; in which the weight ratio of the components (a) and (b) is within a specific range.

SUMMARY OF INVENTION

Technical Problem

However, when the added amount of the photopolymerization initiator is increased in order to enhance the photocurability, yellowing occurs when the composition is cured, resulting in loss of transparency. On the contrary, when the added amount of the photopolymerization initiator is decreased, the curability of the composition is lowered, and thus there is a problem that the glossiness is lowered. Thus, it has been difficult to simultaneously achieve good transparency and glossiness.

The present invention has been made in view of the above circumstances and has an object to provide a photocurable resin composition for a nail or an artificial nail that can form a cured product that has excellent transparency and gloss while having hardness required for coating a nail or an artificial nail. Another object of the present invention is to provide a cured product obtained by curing the photocurable resin composition for a nail or an artificial nail. Still another object of the present invention is to provide a method for coating a nail or an artificial nail using the photocurable resin composition for a nail or an artificial nail.

Solution to Problem

As a result of intensive studies to achieve the above object, the present inventors have found that a photocurable resin composition for a nail or an artificial nail to be described in detail below can form a cured product having excellent transparency and gloss while having hardness required for coating a nail or an artificial nail, and have completed the present invention.

The gist of the present invention will be described below.

[1] A photocurable resin composition for a nail or an artificial nail, including components (A) to (D) below:

component (A): a urethane (meth)acrylate oligomer, component (B): a compound having three or more (meth)acryloyl groups (excluding the component (A)), component (C): a compound having a molecular weight of 200 or less and having a hydroxyl group and a methacryloyl group (excluding the components (A) and (B)), and component (D): a photoinitiator.

[2] The photocurable resin composition for a nail or an artificial nail according to [1], in which the component (B) contains a (meth)acrylate monomer having three or more (meth)acryloyl groups.

[3] The photocurable resin composition for a nail or an artificial nail according to [1] or [2], in which the component (B) contains at least one selected from the group consisting of dipentaerythritol hexaacrylate, dipentaerythritol pentaacrylate, and trimethylolpropane trimethacrylate.

[4] The photocurable resin composition for a nail or an artificial nail according to any one of [1] to [3], in which the component (A) contains a urethane (meth)acrylate oligomer having a polyether skeleton.

[5] The photocurable resin composition for a nail or an artificial nail according to any one of [1] to [4], containing 1 to 50 parts by mass of the component (C) with respect to 100 parts by mass of the component (A).

[6] The photocurable resin composition for a nail or an artificial nail according to any one of [1] to [5], in which the component (D) is an acylphosphine oxide-based photoinitiator and/or an alkylphenone-based photoinitiator.

[7] The photocurable resin composition for a nail or an artificial nail according to any one of [1] to [6], in which the component (C) is a compound having a molecular weight of 100 or more and 200 or less and having a hydroxyl group and a methacryloyl group.

[8] The photocurable resin composition for a nail or an artificial nail according to any one of [1] to [7], in which a yellowness of a cured product of the photocurable resin composition for a nail or an artificial nail is 1.25 or less.

[9] The photocurable resin composition for a nail or an artificial nail according to any one of [1] to [8], used for a top coat.

[10] A cured product of the photocurable resin composition for a nail or an artificial nail set forth in any one of [1] to [9].

[11] A method for coating a nail or an artificial nail, including: applying the photocurable resin composition for a nail or an artificial nail set forth in any one of [1] to [9] on a nail or an artificial nail to form a coating film; and then irradiating the coating film with an active energy ray to cure the coating film.

DESCRIPTION OF EMBODIMENTS

Hereinafter, embodiments of the invention will be described. Note that the present disclosure is not limited only to the following embodiments. In the present specification, "X to Y" means a range including numerical values (X and Y) described before and after the "X to Y" as the lower limit value and the upper limit value. In addition, the concentration and "%" represent a mass concentration and mass %, respectively, unless otherwise specified, and the ratio is a mass ratio unless otherwise specified. In addition, unless otherwise specified, operations and measurements of physical properties and the like are performed under the conditions of room temperature (20 to 25° C.)/relative humidity 40 to 50% RH. In addition, "A and/or B" includes each and a combination of A and B, specifically means at least one of A and B, and means A, B, and a combination of A and B.

Photocurable Resin Composition for Nail or Artificial Nail

The photocurable resin composition for a nail or an artificial nail (hereinafter also referred to as "photocurable resin composition" or simply "composition") according to an embodiment of the present invention includes components (A) to (D) below:

component (A): a urethane (meth)acrylate oligomer,
component (B): a compound having three or more (meth)acryloyl groups (excluding the component (A)),
component (C): a compound having a molecular weight of 200 or less and having a hydroxyl group and a methacryloyl group (excluding the components (A) and (B)), and
component (D): a photoinitiator.

With the photocurable resin composition according to an embodiment of the present invention, a cured product having excellent transparency and gloss can be formed. Furthermore, with the photocurable resin composition according to an embodiment of the present invention, a cured product having such hardness that is required for coating a nail or an artificial nail can be obtained.

Details of this mechanism are unknown, but it is considered that the compound contained as the component (C) particularly contributes to suppression of yellowing (improvement of transparency) and improvement of glossiness in a well-balanced manner. Specifically, when the molecular weight of the compound included as the component (C) exceeds 200, transparency and glossiness (particularly transparency) decrease (Comparative Examples 2 to 4 and the like described later). When the compound does not have a methacryloyl group (for example, it has an acryloyl group instead), the glossiness is particularly likely to decrease (Comparative Examples 1 and 6 described later). When the compound does not have a hydroxyl group, it is difficult to suppress yellowing, and particularly transparency tends to be deteriorated (Comparative Examples 5 to 7 described later).

In addition, the compound contained as the component (B) is considered to contribute to the improvement of the hardness of the cured product. When the photocurable resin composition does not contain a compound corresponding to the component (B), the hardness of the cured product decreases (Comparative Examples 8 to 10 described later).

Note that the above mechanism is based on presumption, and correctness or incorrectness of the mechanism does not affect the technical scope of the present invention.

Component (A)

The component (A) contained in the photocurable resin composition according to the present invention is a urethane (meth)acrylate oligomer. The urethane (meth)acrylate oligomer refers to an oligomer having one or more urethane bonds and one or more (meth)acryloyl groups. By adding the urethane (meth)acrylate oligomer to the photocurable resin composition, an effect of improving adhesion to a nail or an artificial nail and an effect of improving curability and strength of the photocurable resin composition (coating film) are obtained.

In the present specification, for the (meth)acryloyl group, a (meth)acryloyl group may be included as a form of a (meth)acryloyloxy group. Also, the term "(meth)acryloyl" encompasses both acryloyl and methacryloyl. Thus, for example, the term "(meth)acryloyl group" encompasses both an acryloyl group ($H_2C\!=\!CH\!-\!C(\!=\!O)\!-$) and a methacryloyl group ($H_2C\!=\!C(CH_3)\!-\!C(\!=\!O)\!-$). Also, similarly, the term "(meth)acrylate" encompasses both acrylate and methacrylate, and the term "(meth)acrylic" encompasses both acrylic and methacrylic. The term "oligomer" refers to a polymer in which monomer units (including monomer units other than (meth)acrylate monomers) are repeated about two to several tens of times.

The component (A) is not particularly limited as long as it is an oligomer having one or more urethane bonds and one or more (meth)acryloyl groups. In addition, a compound having a urethane bond in addition to three or more (meth) acryloyl groups (note that it is an oligomer) is included in the component (A) and is not included in the component (B).

The number of (meth)acryloyl groups contained in the oligomer of the component (A) is not particularly limited as long as it is one or more, but it is preferable to contain two to six (meth)acryloyl groups (bi- to hexafunctional (meth) acrylate oligomer), and it is more preferable to have two (meth)acryloyl groups (bifunctional (meth)acrylate oligomer). The (meth)acryloyl group of the component (A) is preferably an acryloyl group. In addition to the urethane bond and the (meth)acryloyl group, the component (A) may have other functional groups such as a carboxy group, a phosphate group, an epoxy group, a hydroxyl group, or the like.

The weight average molecular weight of the oligomer of the component (A) is preferably 1,000 to 100,000, more preferably 2,000 to 30,000, particularly preferably 3,000 to 20,000. Within such a range, the curability of the cured product can be made good while maintaining such a viscosity as to provide good workability. In the present specification, for the weight average molecular weight, a value measured by gel permeation chromatography (GPC) using polystyrene as a standard substance is employed.

As the urethane (meth)acrylate oligomer as the component (A), either a synthetic product or a commercially available product may be used. The urethane (meth)acrylate oligomer as the component (A) can be produced by a conventionally known method or by appropriately modifying such methods. As a method for synthesizing the urethane (meth)acrylate oligomer, for example, the synthesis can be performed by forming a urethane bond by a reaction between a polyol and a polyisocyanate and adding a compound having a hydroxyl group and a (meth)acryloyl group in the molecule or (meth)acrylic acid to an unreacted isocyanate group, but the method for synthesizing the urethane (meth)acrylate oligomer is not limited to this method.

In particular, from the viewpoint of adhesion to a nail or an artificial nail, the component (A) preferably contains a urethane (meth)acrylate oligomer having a polyether skeleton. Specifically, it is preferable to use a urethane (meth) acrylate oligomer having a polyether skeleton which is obtained by using an aliphatic polyether polyol or an aromatic polyether polyol having a bisphenol skeleton or the like as the above polyol used in production of the urethane (meth)acrylate oligomer. However, other urethane (meth) acrylate oligomers such as a polyester skeleton-containing urethane (meth)acrylate oligomer, a polycaprolactone skeleton-containing urethane (meth)acrylate oligomer, a polycarbonate skeleton-containing urethane (meth)acrylate oligomer, or the like can also be used in combination as the component (A).

Specific examples of commercially available products of oligomers of the component (A) include, but are not limited to, AH-600 and UA-510H (manufactured by Kyoeisha Chemical Co., Ltd.), SUA-008 and SUA-023 (manufactured by Asia Industry Co., Ltd.), UN-6060S, UN-606OPTM, UN-6200, UN-6207, UN-6303, UN-6304, UN-6305, and UN-6306 (manufactured by Negami Chemical Industrial Co., Ltd.), and the like.

In addition, the urethane (meth)acrylate oligomer as the component (A) may be used alone or may be used in combination of two or more thereof. When two or more kinds are used in combination, the content of the component (A) refers to the total amount.

<Component (B)>

The component (B) contained in the photocurable resin composition according to the present invention is a compound having three or more (three functional groups or more) (meth)acryloyl groups (excluding the component (A)).

By adding a compound having three or more (meth) acryloyl groups to the photocurable resin composition, a cured product having such hardness that is required for coating a nail or an artificial nail can be obtained.

Regarding the compound used as a component (B), the number of (meth)acryloyl groups contained in one molecule is not particularly limited as long as it is three or more. In addition, a compound having a molecular weight of 200 or less and having one or more hydroxyl groups and three or more methacryloyl groups is included in the component (B) and is not included in the component (C).

The number of (meth)acryloyl groups contained in the compound of the component (B) is not particularly limited as long as it is three or more but is preferably three to eight (tri- to octafunctional), more preferably three to six (tri- to hexafunctional), still more preferably four to six (tetra- to hexafunctional), particularly preferably five or six (penta- or hexafunctional), for the purpose of obtaining a cured product having good hardness. From the viewpoint of effectively suppressing yellowing of the cured product, the number of (meth)acryloyl groups contained in one molecule is preferably three or four (tri- or tetrafunctional), more preferably three (trifunctional).

In addition, for the purpose of obtaining a cured product having good hardness, the (meth)acryloyl group contained in the compound of the component (B) is preferably an acryloyl group. On the other hand, from the viewpoint of effectively suppressing yellowing of the cured product, the (meth)acryloyl group contained in the compound of the component (B) is preferably a methacryloyl group.

From the viewpoint of being capable of obtaining a photocurable resin composition excellent in curability, the component (B) preferably contains an ester monomer having three or more (meth)acryloyl groups (that is, the (meth) acrylate monomer). The preferable number of (meth)acryloyl groups contained in the (meth)acrylate monomer is the same as described above.

The molecular weight of the compound of the component (B) is not particularly limited but is preferably less than 1,000, more preferably 600 or less, from the viewpoint of improving the curability of the photocurable resin composition. From the viewpoint of excellent compatibility with the component (A), the molecular weight of the compound of the component (B) is preferably more than 200, more preferably 300 or more. In the present specification, the molecular weight of a compound (low molecular weight compound) can be measured by a known method such as a gas chromatography-mass spectrometry (GC-MS) method, or the like. In addition, the molecular weight can also be determined by identifying the structure of the compound by a method such as NMR or the like and performing calculation based on the identified structure.

Specific examples of the component (B) contained in the photocurable resin composition according to the present invention include trifunctional (meth)acrylate monomers such as trimethylolpropane tri(meth)acrylate, trimethylolethane tri(meth)acrylate, ethoxylated trimethylolpropane tri (meth)acrylate, isocyanuric acid ethylene oxide—(hereinafter referred to as EO) modified tri(meth)acrylate, pentaerythritol tri(meth)acrylate, EO-modified trimethylolpropane tri(meth)acrylate, propylene oxide—(hereinafter referred to as PO) modified trimethylolpropane tri(meth) acrylate, epichlorohydrin—(ECH) modified trimethylolpropane tri(meth)acrylate, ECH-modified glycerol tri(meth) acrylate, tris(acryloyloxyethyl)isocyanurate, or the like; tetrafunctional (meth)acrylate monomers such as pentaerythritol tetra(meth)acrylate, tetramethylolmethane tetra (meth)acrylate, dipentaerythritol tetra(meth)acrylate, and di-trimethylolpropane tetra(meth)acrylate, or the like; pentafunctional (meth)acrylate monomers such as dipentaerythritol penta(meth)acrylate and caprolactone-modified pentaerythritol penta(meth)acrylate, or the like; hexafunctional (meth)acrylate monomers such as dipentaerythritol hexa(meth)acrylate and caprolactone-modified pentaerythritol hexa(meth)acrylate, or the like; and the like. Among them, dipentaerythritol hexaacrylate, dipentaerythritol pentaacrylate, and trimethylolpropane trimethacrylate are preferable. That is, the component (B) preferably contains at least one selected from the group consisting of dipentaerythritol hexaacrylate, dipentaerythritol pentaacrylate, and trimethylolpropane trimethacrylate. As the component (B), a single kind or a combination of two or more kinds can be used. When two or more kinds are used in combination, the content of the component (B) refers to the total amount.

In the photocurable resin composition according to the present invention, the content of the component (B) is preferably 20 to 80 parts by mass, more preferably 30 to 70 parts by mass, relative to 100 parts by mass of the component (A). From the viewpoint of the hardness of the cured product formed from the photocurable resin composition, the content of the component (B) is still more preferably 40 to 60 parts by mass relative to 100 parts by mass of the component (A). When the component (B) is 20 parts by mass or more relative to 100 parts by mass of the component (A), the hardness of the cured product can be favorably maintained. On the other hand, when (B) is 80 parts by mass or less, the transparency of the cured product can be favorably maintained.

Component (C)

The component (C) contained in the photocurable resin composition according to the present invention is a compound having a molecular weight of 200 or less and having a hydroxyl group and a methacryloyl group (excluding the component (A) and the component (B)).

By adding the compound to the photocurable resin composition, both transparency and glossiness of the cured product can be improved in a well-balanced manner.

The molecular weight of the compound used as the component (C) is not particularly limited as long as it is 200 or less, but is preferably 100 or more and 200 or less, more preferably 100 or more and 180 or less, particularly preferably 100 or more and 150 or less, from the viewpoint of transparency.

The compound of the component (C) may have two or more hydroxyl groups and/or two or more methacryloyl groups. However, from the viewpoint of transparency, the number of hydroxyl groups and the number of methacryloyl groups contained in the compound of the component (C) are each preferably two or less. From the same viewpoint as described above, the number of hydroxyl groups and the number of methacryloyl groups contained in the compound of the component (C) are each more preferably one.

In addition to the hydroxyl group and the methacryloyl group, the compound of the component (C) may have a carboxy group, a phosphate group, an epoxy group, and other functional group. The "hydroxyl group" contained in the component (C) does not include "—OH" contained in an oxo acid group such as a carboxy group, a phosphate group, or the like.

From the viewpoint of being capable of obtaining a photocurable resin composition excellent in curability, the component (C) preferably contains an ester monomer having a molecular weight of 200 or less and having a hydroxyl group and a methacryloyl group (that is, the methacrylate monomer). A preferable molecular weight of the methacrylate monomer and a preferable number of methacryloyl groups contained therein are the same as described above.

The hydroxyl group contained in the compound of the component (C) is preferably contained as an alcohol skeleton or a phenol skeleton. The position of substitution with the hydroxyl group is not particularly limited, and the hydroxyl group may be present at the terminal of the compound or may be present as a side chain (on a side chain). From the viewpoint of transparency, the hydroxyl group contained in the compound of the component (C) is preferably contained as a side chain (on a side chain) of the compound.

In other words, the hydroxyl group contained in the compound of the component (C) may be any of a primary hydroxyl group, a secondary hydroxyl group, and a tertiary hydroxyl group. Among them, from the viewpoint of transparency, a secondary hydroxyl group or a tertiary hydroxyl group is preferable, and a secondary hydroxyl group is more preferable. That is, from the viewpoint of transparency, the compound of the component (C) is preferably a secondary alcohol or a tertiary alcohol, more preferably a secondary alcohol.

Specific examples of the component (C) contained in the photocurable resin composition according to the present invention include, but are not limited to, 2-hydroxyethyl methacrylate (primary alcohol), 2-hydroxypropyl methacrylate (secondary alcohol), 2-hydroxybutyl methacrylate (secondary alcohol), 3-hydroxy-3-methylbutyl methacrylate (tertiary alcohol), 2-hydroxypentyl methacrylate (secondary alcohol), 5-hydroxypentyl methacrylate (primary alcohol), 6-hydroxyhexyl methacrylate (primary alcohol), 2-hydroxyheptyl methacrylate (secondary alcohol), 7-hydroxyoctyl methacrylate (secondary alcohol), and the like. As the component (C), a single kind or a combination of two or more kinds can be used. When two or more kinds are used in combination, the content of the component (C) refers to the total amount.

In the photocurable resin composition according to the present invention, the content of the component (C) is preferably 1 to 50 parts by mass, more preferably 5 to 45 parts by mass, relative to 100 parts by mass of the component (A). From the viewpoint of the transparency of the cured product formed from the photocurable resin composition, the content of the component (C) is still more preferably 10 to 40 parts by mass, particularly preferably 15 to 30 parts by mass, relative to 100 parts by mass of the component (A). When the component (C) is 1 part by mass or more relative to 100 parts by mass of the component (A), the glossiness of the cured product can be favorably maintained. On the other hand, when the component (C) is 50 parts by mass or less, the transparency of the cured product can be favorably maintained.

Component (D)

The component (D) contained in the photocurable resin composition according to the present invention is a photoinitiator (photopolymerization initiator). Examples of the component (D) include a radical photoinitiator that generates radical species by irradiation with active energy rays such as visible rays, ultraviolet rays, X-rays, electron beams, and the like; a cationic photoinitiator that generates cationic species; and an anionic photogenerator that generates anionic species, and among them, a radical photoinitiator is preferable.

Examples of the radical photoinitiator include alkylphenone-based compounds, acylphosphine oxide-based compounds, titanocene-based compounds, oxime ester-based compounds, benzoin-based compounds, acetophenone-based compounds, benzophenone-based compounds, thioxanthone-based compounds, α-acyloxime ester-based compounds, phenylglyoxylate-based compounds, benzyl-based compounds, azo-based compounds, diphenyl sulfide-based compounds, organic dye-based compounds, iron-phthalocyanine-based compounds, benzoin ether-based compounds, anthraquinone-based compounds, and the like. Among them, an alkylphenone-based compound and an acylphosphine oxide-based compound are preferable from the viewpoint of reactivity and the like. That is, the component (D) is preferably an acylphosphine oxide-based photoinitiator and/or an alkylphenone-based photoinitiator.

Examples of the alkylphenone-based compound include 1-hydroxycyclohexyl phenyl ketone, 2-hydroxy-2-methyl-1-phenyl-propane-1-one, α-aminoalkylphenone, and the like, and examples of the acylphosphine oxide-based compound include 2,4,6-trimethylbenzoyl-diphenyl-phosphine oxide, bis(2,4,6-trimethylbenzoyl)-phenylphosphine oxide, and the like. As the component (D), a single kind or a combination of two or more kinds can be used. When two or more kinds are used in combination, the content of the component (D) refers to the total amount.

From the viewpoint of achieving both glossiness and transparency, an alkylphenone-based compound and an acylphosphine oxide-based compound are preferably used in combination as the component (D). That is, the component (D) preferably contains an acylphosphine oxide-based photoinitiator and an alkylphenone-based photoinitiator.

In the photocurable resin composition according to the present invention, the content of the component (D) is preferably 0.1 to 15 parts by mass, more preferably 1 to 12 parts by mass, still more preferably 3 to 9 parts by mass, relative to 100 parts by mass of the component (A). When the component (D) is 0.1 parts by mass or more relative to 100 parts by mass of the component (A), the glossiness of the cured product can be favorably maintained. On the other hand, when the component (D) is 15 parts by mass or less, the transparency of the cured product can be favorably maintained.

Optional Component

The photocurable resin composition according to the present invention may further contain additives such as a compound having a (meth)acryloyl group (excluding the components (A) to (C)), a filler, a conductive filler, a silane coupling agent, a plasticizer, an adhesive, an antifoaming agent, a pigment, a rust inhibitor, a leveling agent, a dispersant, a rheology modifier, a flame retardant, and the like in addition to the above components (A) to (D) as long as the object of the present invention is not impaired.

Examples of the compound having a (meth)acryloyl group, which can be contained in addition to the component (A), the component (B), and the component (C) in the photocurable resin composition according to the present invention, include monofunctional (meth)acrylate compounds, bifunctional (meth)acrylate compounds, and the like listed below.

Specific examples of the (meth)acrylate compound having one (meth)acryloyl group (monofunctional (meth)acrylate compound) other than the component (A), the component (B), and the component (C) include, but are not limited to, lauryl (meth)acrylate, stearyl (meth)acrylate, ethyl carbitol (meth)acrylate, tetrahydrofurfuryl (meth)acrylate, caprolactone-modified tetrahydrofurfuryl (meth)acrylate, cyclohexyl (meth)acrylate, dicyclopentanyl (meth)acrylate, isobornyl (meth)acrylate, benzyl (meth)acrylate, phenyl (meth)acrylate, phenoxyethyl (meth)acrylate, phenoxydiethylene glycol (meth)acrylate, phenoxytetraethylene glycol (meth)acrylate, nonylphenoxyethyl (meth)acrylate, nonylphenoxytetraethylene glycol (meth)acrylate, methoxydiethylene glycol (meth)acrylate, ethoxydiethylene glycol (meth)acrylate, butoxyethyl (meth)acrylate, butoxytriethylene glycol (meth)acrylate, 2-ethylhexylpolyethylene glycol (meth)acrylate, 4-hydroxybutyl acrylate, nonylphenylpolypropylene glycol (meth)acrylate, methoxydipropylene glycol (meth)acrylate, 2-hydroxyethyl acrylate, 2-hydroxypropyl acrylate, glycerol (meth)acrylate, polyethylene glycol (meth)acrylate, polypropylene glycol (meth)acrylate, epichlorohydrin-modified butyl (meth)acrylate, epichlorohydrin-modified phenoxy (meth)acrylate, N,N-dimethylaminoethyl (meth)acrylate, N,N-diethylaminoethyl (meth) acrylate, and the like.

Specific examples of the (meth)acrylate compound having two (meth)acryloyl groups (bifunctional (meth)acrylate compound) other than the component (A), the component (B), and the component (C) include, but are not limited to, 1,3-butylene glycol di(meth)acrylate, 1,4-butylene glycol di(meth)acrylate, tricyclodecane dimethanol di(meth)acrylate, neopentyl glycol di(meth)acrylate, 1,6-hexane glycol di(meth)acrylate, ethylene glycol diacrylate, tetraethylene glycol di(meth)acrylate, polyethylene glycol di(meth)acrylate, propylene glycol di(meth)acrylate, tripropylene glycol di(meth)acrylate, ethylene oxide-modified neopentyl glycol di(meth)acrylate, propylene oxide-modified neopentyl glycol di(meth)acrylate, bisphenol A di(meth)acrylate, ethylene oxide-modified bisphenol A di(meth)acrylate, epichlorohydrin-modified bisphenol A di(meth)acrylate, ethylene oxide-modified bisphenol S di(meth)acrylate, neopentyl glycol-modified trimethylolpropane di(meth)acrylate, dicyclopentenyl di(meth)acrylate, ethylene oxide-modified dicyclopentenyl di(meth)acrylate, diacryloyl isocyanurate, and the like.

The photocurable resin composition according to the present invention may further contain a filler in addition to the above components (A) to (D) as long as the object of the present invention is not impaired, for the purpose of improving the elastic modulus, fluidity, and the like of the cured product. Examples of the filler include inorganic powder, organic powder, and the like.

Examples of the filler of the inorganic powder include, but are not limited to, glass, fumed silica, alumina, mica, ceramics, silicone rubber powder, calcium carbonate, aluminum nitride, carbon powder, kaolin clay, dry clay mineral, dry diatomaceous earth, kaolin, and the like. These may be used alone or in combination of two or more kinds. The blending amount (if two or more kinds are included, the total amount thereof) of the inorganic powder is preferably about 0.1 to 200 parts by mass relative to 100 parts by mass of the component (A).

Fumed silica can be blended for the purpose of adjusting the viscosity of the photocurable resin composition or improving the mechanical strength of the cured product. Preferably, fumed silica surface-treated with dimethylsilane, trimethylsilane, alkylsilane, methacryloyloxysilane, organochlorosilane, polydimethylsiloxane, hexamethyldisilazane, or the like is used. Examples of commercially available products of fumed silica include, but are not limited to, AEROSIL (registered trademark) R 972, R 972 V, R 972 CF, R 974, R 976, R 976 S, R 9200, RX 50, NAX 50, NX 90, RX 200, RX 300, R 812, R 812 S, R 8200, RY 50, NY 50, RY 200 S, RY 200, RY 300, R 104, R 106, R 202, R 805, R 816, T 805, R 711, R 7200, and the like (manufactured by Nippon Aerosil Co., Ltd.). These may be used alone or in combination of two or more kinds.

Examples of the filler of the organic powder include, but are not limited to, polyethylene, polypropylene, polystyrene, nylon, polyester, polyvinyl alcohol, polyvinyl butyral, polycarbonate, and polymethyl (meth)acrylate. These may be used alone or in combination of two or more kinds. The blending amount (if two or more kinds are included, the total amount thereof) of the organic powder is preferably about 0.1 to 200 parts by mass relative to 100 parts by mass of the component (A).

The photocurable resin composition according to the present invention may further contain a conductive filler in addition to the above components (A) to (D) as long as the object of the present invention is not impaired. Examples of the conductive filler include, but are not limited to, gold, silver, platinum, nickel, palladium, and plated particles in which organic polymer particles are coated with a thin metal film. These may be used alone or in combination of two or more kinds.

The photocurable resin composition according to the present invention may further contain a silane coupling agent in addition to the above components (A) to (D) as long as the object of the present invention is not impaired. Examples of the silane coupling agent include, but are not limited to, γ-chloropropyltrimethoxysilane, octenyltrimethoxysilane, glycidoxyoctyltrimethoxysilane, β-(3,4-epoxycyclohexyl)ethyltrimethoxysilane, γ-glycidoxypropyltrimethoxysilane, γ-mercaptopropyltrimethoxysilane, γ-aminopropyltriethoxysilane, N-β-(aminoethyl)-γ-aminopropyltrimethoxysilane, N-β-(aminoethyl)-γ-aminopropylmethyldimethoxysilane, γ-ureidopropyltriethoxysilane, p-styryltrimethoxysilane, and the like. These may be used alone or in combination of two or more kinds. The content (if two or more kinds are included, the total amount thereof) of the silane coupling agent is preferably 0.05 to 30 parts by mass, more preferably 0.2 to 10 parts by mass, relative to 100 parts by mass of the component (A).

A method for producing the photocurable resin composition according to the present invention is not particularly limited, and the photocurable resin composition can be produced by a conventionally known method. For example, the photocurable resin composition according to the present invention can be obtained by respectively weighing predetermined amounts of the component (A) to component (D) and optionally added components (optional components), adding them sequentially or simultaneously regardless of the order to a mixing pot, and then mixing them using mixing means such as a planetary mixer, or the like. At this time, the production conditions are not particularly limited, but for the purpose of suppressing an increase in viscosity, the production is preferably performed under light-shielding conditions, the mixing temperature is preferably 10 to 50° C., and the mixing time is preferably 0.1 to 5 hours.

Cured Product

Another embodiment of the present invention is a cured product obtained by curing the photocurable resin composition (cured product of the photocurable resin composition). Here, specific examples of the cured product include a top coat used for nail color art.

The cured product according to the present invention has excellent transparency and gloss while having hardness required for coating a nail or an artificial nail. Specifically, for a cured product obtained by curing the photocurable resin composition according to the present invention, the hardness measured by the method described in Examples is preferably 70 or more (D 70 or more). The cured product preferably has a yellowness of 1.25 or less as measured by the method described in Examples. Furthermore, for the cured product, it is preferable that the glossiness measured by the method described in Examples be 80 or more at 60° and 70 or more at 20°.

A method for producing the cured product (such as a top coat or the like) of the photocurable resin composition is not particularly limited, and a known method can be used. Among them, a method of curing the photocurable resin composition using an active energy ray is preferable. That is, the present invention also provides a method for producing a cured product, the method including irradiating the photocurable resin composition with an active energy ray to cure the photocurable resin composition.

The method for producing the cured product is not particularly limited, and a known method can be used. As an example, there is a method in which the photocurable resin composition according to the present invention is applied on a nail (natural nail) or a preformed artificial nail (nail chip) and then cured by irradiation with an active energy ray (light or the like). As another example, the photocurable resin composition according to the present invention may be formed into a desired shape and then cured with irradiation with an active energy ray (light or the like).

Irradiation light used for irradiation with an active energy ray is not particularly limited, but irradiation light in a wavelength range of 200 to 750 nm is usually preferable. The irradiation device is not particularly limited, and a known device can be used according to a desired wavelength, and examples thereof include a low-pressure mercury lamp, a medium-pressure mercury lamp, a high-pressure mercury lamp, a xenon lamp, a metal halide lamp, an LED lamp, and the like. Among them, a high-pressure mercury lamp or an LED lamp is preferable from the viewpoint of curability, curing efficiency, and the like.

The irradiation time of the active energy ray is not particularly limited, but for example, in the case where an LED lamp is used, it is preferably 15 to 120 seconds, more preferably 20 to 70 seconds. In addition, the integrated light amount is preferably 200 to 5,000 mJ/cm$^2$, more preferably 300 to 1,500 mJ/cm$^2$, particularly preferably 500 to 1,000 mJ/cm$^2$. At the time of curing, irradiation with an active energy ray may be performed a plurality of times as necessary.

Method for Covering (Decorating) Nail or Artificial Nail

Another embodiment of the present invention is a method for coating a nail or an artificial nail, including: applying the photocurable resin composition on a nail or an artificial nail to form a coating film; and then irradiating the coating film with an active energy ray to cure the coating film. Note that, in the present specification, "applied on (onto) a nail or an artificial nail" includes a form of being applied directly to a surface of a human nail (natural nail) or an artificial nail (nail chip) and a form of being applied to an outermost surface of a single or a plurality of other layers formed on a surface of a human nail or an artificial nail.

That is, a preferable embodiment of the present invention is a method for coating a nail or an artificial nail, including applying a photocurable resin composition containing components (A) to (D) below for a nail or an artificial nail on a nail (natural nail) or an artificial nail to form a coating film; and then irradiating the coating film with an active energy ray to cure the coating film:

component (A): a urethane (meth)acrylate oligomer,
component (B): a compound having three or more (meth)acryloyl groups (excluding the component (A)),
component (C): a compound having a molecular weight of 200 or less and having a hydroxyl group and a methacryloyl group (excluding the components (A) and (B)), and
component (D): a photoinitiator.

The artificial nail in the present invention refers to a layer formed on a human or animal nail for the purpose of decoration and/or protection. The artificial nail also includes a resin base material (nail extension) or the like having any shape for the purpose of decoration and/or protection of the nail. In addition, the shape of the artificial nail is not particularly limited, and the artificial nail may be formed so as to cover the nail, or it may be formed larger than a nail for the purpose of extending the nail. In addition, the artificial nail may be formed for the purpose of bonding an item (decoration) such as a stone or the like to the nail to improve the aesthetic appearance.

The configuration of an artificial nail generally has a configuration in which a base coat layer (layer for imparting adhesion to a nail, preventing color migration, and the like), a color layer (layer for decoration, including a coloring material and the like), and a top coat layer (layer for coating, imparting gloss, and improving aesthetic appearance) are laminated in this order. Further, in the forming method, first, a base coat layer formed by curing a photocurable resin composition for a base coat is formed on the surface of a nail, a color layer formed by curing a photocurable resin composition for coloring is formed thereon, and a top coat layer formed by curing a photocurable resin composition for a top coat is further formed thereon. The photocurable resin composition according to the present invention is not particularly limited as long as it is used for the purpose of forming a layer on a nail or an artificial nail, but it is preferably used as a photocurable resin composition for a top coat because it has good glossiness and transparency in a well-balanced manner. That is, the photocurable resin composition according to the present invention is preferably for a top coat.

The method for applying the photocurable resin composition and the method for curing the coating film (applied photocurable resin composition) are not particularly limited and can be performed by methods known to those skilled in the art. In addition, the description related to the method for producing a cured product described in the above section [Cured Product] is also applicable.

A preferable example of a method for covering (decorating) a nail or an artificial nail according to the present invention is shown below, but the method according to the present invention is not limited to this method.

When the photocurable resin composition according to the present invention is directly applied to a nail, the following operation is preferably performed as necessary in order to improve adhesion of a coating film. That is, it is preferable to perform sanding of the surface of the nail with a file (rasp) or the like before applying the photocurable resin composition. Thereafter, it is preferable to remove dust, oil, moisture, and the like with a solvent for nails containing ethanol as a main component. Next, the photocurable resin composition according to the present invention is applied on the nail so as to form a coating film having a thickness of 50 to 300 µm in a state before curing with a paintbrush, a brush, or the like (formation of a coating film). In addition, a coating film may be formed by applying the photocurable resin composition according to the present invention on another layer (a cured film of a base coating resin, a cured film of a coloring resin) formed in advance. In addition, a primer may be used in advance at the time of application.

After the coating film is formed by applying the photocurable resin composition as described above, the coating film is irradiated with an active energy ray to cure the coating film (applied photocurable resin composition). The irradiation device of the active energy ray at the time of curing is not particularly limited, but commercially available UV lamps for nails, LED lamps for nails, and the like can be used. The irradiation time of the active energy ray is preferably 15 to 120 seconds, more preferably 20 to 70 seconds in consideration of the influence on the finger. In addition, the integrated light amount is preferably 200 to 5,000 $mJ/cm^2$, more preferably 300 to 1,500 $mJ/cm^2$, particularly preferably 500 to 1,000 $mJ/cm^2$. At the time of curing, irradiation with an active energy ray may be performed a plurality of times as necessary.

EXAMPLES

Hereinafter, the present invention will be described in more detail with reference to Examples, but the scope of the present invention is not limited to these Examples. In the following Examples, unless otherwise specified, operations were performed at room temperature (25° C.). Hereinafter, the photocurable resin composition for a nail or an artificial nail is also simply referred to as a "photocurable resin composition" or a "resin".

Preparation of Photocurable Resin Composition

The following components were each weighed in a proportion (unit: part by mass) shown in Table 1 and mixed for 60 minutes using a planetary mixer under a 25° C. environment and light-shielding conditions to prepare a photocurable resin composition. Details of each component are as follows.

Component (A)

a1: Polyether skeleton-containing bifunctional urethane acrylate (ART RESIN UN-6303, manufactured by Negami Chemical Industrial Co., Ltd., weight average molecular weight: 4,000, acrylate oligomer having acryloyl groups at each terminal of the molecular chain)

Component (B)

b1: Mixture of dipentaerythritol hexaacrylate (number of acryloyl groups: 6; molecular weight: 579; 60 mass % relative to 100 mass % of the mixture) and dipentaerythritol pentaacrylate (number of acryloyl groups: 5; molecular weight: 525; 40 mass % relative to 100 mass % of the mixture) (KAYARAD DPHA, manufactured by Nippon Kayaku Co., Ltd.)

b2: Trimethylolpropane trimethacrylate (NK ESTER TMPT, manufactured by Shin-Nakamura Chemical Co., Ltd.; number of methacryloyl groups: 3; molecular weight: 338)

Component (C)

c1: 2-Hydroxypropyl methacrylate (HPMA, manufactured by Nippon Shokubai Co., Ltd., molecular weight: 144)

c2: 2-Hydroxybutyl methacrylate (Light Ester HOB (N), manufactured by Kyoeisha Chemical Co., Ltd., molecular weight: 158)

Comparative Examples of Component (C)

c'1: 4-Hydroxybutyl acrylate (4-HBA, manufactured by Osaka Organic Chemical Industry Ltd., molecular weight: 144)

c'2: 2-Methacryloyloxyethyl acid phosphate (2-Hydroxyethyl methacrylate phosphate) (Light Ester P-2M, manufactured by Kyoeisha Chemical Co., Ltd., molecular weight: 228)

c'3: 2-Methacryloyloxyethyl succinate (Light Ester HO-MS (N), manufactured by Kyoeisha Chemical Co., Ltd., molecular weight: 230)

c'4: Glycerin dimethacrylate (Light Ester G-101P, manufactured by Kyoeisha Chemical Co., Ltd., molecular weight: 228)

c'5: Isobornyl methacrylate (Acrylic Ester IBX (IBXMA), manufactured by Mitsubishi Chemical Corporation, molecular weight: 222)

c'6: Isobornyl acrylate (IBXA, manufactured by Osaka Organic Chemical Industry Ltd., molecular weight: 208)

c'7: 2-Ethylhexyl methacrylate (Light Ester EH, manufactured by Kyoeisha Chemical Co., Ltd., molecular weight: 198)

Component (D)

d1: 1-Hydroxycyclohexyl phenyl ketone (DOUBLE-CURE (registered trademark) 184, manufactured by Double bond Chemical Ind., Co., Ltd.)

d2: 2,4,6-Trimethylbenzoyl-diphenyl-phosphine oxide (DOUBLECURE (registered trademark) TPO, manufactured by Double bond Chemical Ind., Co., Ltd.)

Evaluation

The photocurable resin compositions of Examples and Comparative Examples in Table 1 were evaluated by the following test method.

Yellowness (Transparency)

Spacers were set at both ends of alkali-free glass plate having a size of a 0.7×50×50 mm (Corning EAGLE XG (registered trademark)) so that the film thickness was about 0.1 mm, and about 1.5 to 2 g of the photocurable resin composition was applied on the glass plate. Then, another alkali-free glass plate was stacked on the above glass plate and the four corners were pinched to prevent air bubbles from entering the measurement area. The applied photocurable resin composition was allowed to stand for about one minute until the thickness was stabilized, and the protruding resin was wiped off. Thereafter, the photocurable resin composition was cured using an LED lamp for a nail (Lxia EX, 30 W, wavelengths of 395 to 405 nm) to produce two cured products for measurement (curing conditions: irradiation time 30 seconds, integrated light amount 750 mJ/cm$^2$). When two hours (to prevent fading over time) had elapsed after curing, the absorbance of the two cured products for measurement was measured under the following measurement conditions using an ultraviolet-visible spectrophotometer (UV-VIS). Thereafter, on the basis of JIS K 7373: 2006, the yellowness was calculated using an Excel macro file for calculating the yellowness (YI value), and the average value of the two cured products was taken as the yellowness. The yellowness was calculated using D 65 as the standard light. The yellowness measured by the above procedure is preferably 1.25 or less, more preferably 1.20 or less, particularly preferably 1.00 or less. On the other hand, the lower limit thereof is not particularly limited but is substantially 0.01 or more.

Measurement Conditions of Ultraviolet-Visible Spectrophotometer (UV-VIS))

Measurement range: 300 to 800 nm

Scan speed: high speed

Sampling pitch: 1.0

Slit width: 0.5 mm

The baseline measurement was performed with air, and the measurement was performed with one sheet of alkali-free glass set on the reference side.

Glossiness

The surface of a black test piece (with one surface coated with amino-alkyd clear after electrodeposition, material: cold-rolled steel sheet (SPCC-SD)) having a size of 0.8× 70×150 mm was degreased and washed, then a spacer was set so that the film thickness was 0.1 mm, about 2 to 3 ml of the photocurable resin composition was applied, and squeegeeing was performed using a glass rod (uniformly spread). Thereafter, the photocurable resin composition was cured using an LED lamp for a nail (Lxia EX, 30 W, wavelengths of 395 to 405 nm) to produce a cured product for measurement (curing conditions: irradiation time 30 seconds, integrated light amount 750 mJ/cm$^2$). The values at 60° and 20° were measured using a gloss meter (Glossy Checker, manufactured by Horiba, Ltd.). The glossiness measured by the above procedure is preferably 80 or more at 60° and 70 or more at 20°. Furthermore, the glossiness is more preferably 85 or more at 60° and 75 or more at 20°. On the other hand, the upper limit thereof is not particularly limited but is substantially 90 or less at 60° and 88 or less at 20°. In Table 1 below, the glossiness is described as "value at 60°/value at 20°".

Hardness

A spacer having a thickness of 1 mm was placed on a soda-lime glass plate having a size of 3.0×150×150 mm, and the photocurable resin composition was applied. A PET film was stacked thereon, another sheet of soda-lime glass was further stacked thereon to sandwich the photocurable resin composition, using a high-pressure mercury lamp (curing condition: integrated light amount: 30 kJ/m$^2$), the two sheets of soda-lime glass were irradiated once each from the front surface and the back surface, twice in total, to produce a cured product having a thickness of 1 mm (the UV light transmitted through the PET film and soda-lime glass was adjusted so as to be in the above curing conditions, and curing was performed). Three cured products were prepared in the same manner as described above and left for two hours. Thereafter, the soda-lime glass and the PET film were peeled off, and three sheets of the cured product sheet having a thickness of 1 mm were stacked with the surface to which the PET film was attached facing upward. The hardness of the layered cured product sheet was measured on a smooth surface. At this time, the hardness was measured according to JIS K 7215: 1986 using a type D durometer tester under the following measurement conditions. The measurement was performed five times, and an average value of three times excluding the maximum value and the minimum value was determined. The hardness measured by the above procedure is preferably 70 or more, more preferably 75 or more, particularly preferably 80 or more. On the other hand, the upper limit thereof is not particularly limited but is substantially 100 or less.

(Type D Durometer Tester Measurement Conditions)

Durometer pressing speed: 3.0 mm/sec

Reading method of numerical value: maximum value within one second.

TABLE 1

| | Example 1 | Example 2 | Example 3 | Comparative Example 1 | Comparative Example 2 | Comparative Example 3 | Comparative Example 4 |
|---|---|---|---|---|---|---|---|
| a1 | 100 | 100 | 100 | 100 | 100 | 100 | 100 |
| b1 | 50 | 50 | | 50 | 50 | 50 | 50 |
| b2 | | | 50 | | | | |
| c1 | 25 | | 25 | | | | |
| c2 | | 25 | | | | | |
| c'1 | | | | 25 | | | |
| c'2 | | | | | 25 | | |
| c'3 | | | | | | 25 | |
| c'4 | | | | | | | 25 |
| c'5 | | | | | | | |
| c'6 | | | | | | | |
| c'7 | | | | | | | |
| d1 | 5.3 | 5.3 | 5.3 | 5.3 | 5.3 | 5.3 | 5.3 |
| d2 | 2.2 | 2.2 | 2.2 | 2.2 | 2.2 | 2.2 | 2.2 |
| Total | 182.5 | 182.5 | 182.5 | 182.5 | 182.5 | 182.5 | 182.5 |
| Yellowness | 1.19 | 1.25 | 0.94 | 0.95 | 1.40 | 1.35 | 1.33 |
| Glossiness | 88/78 | 86/73 | 83/72 | 61/15 | 85/74 | 85/63 | 86/74 |
| Hardness | D82 | D81 | D77 | D78 | D83 | D82 | D83 |

| | Comparative Example 5 | Comparative Example 6 | Comparative Example 7 | Comparative Example 8 | Comparative Example 9 | Comparative Example 10 |
|---|---|---|---|---|---|---|
| a1 | 100 | 100 | 100 | 100 | 100 | 100 |
| b1 | 50 | 50 | 50 | | | |
| b2 | | | | | | |
| c1 | | | | 25 | | |
| c2 | | | | | | |
| c'1 | | | | | | |
| c'2 | | | | | | |
| c'3 | | | | | | |
| c'4 | | | | | | |
| c'5 | 25 | | | | 25 | |
| c'6 | | 25 | | | | 25 |
| c'7 | | | 25 | | | |
| d1 | 5.3 | 5.3 | 5.3 | 5.3 | 5.3 | 5.3 |
| d2 | 2.2 | 2.2 | 2.2 | 2.2 | 2.2 | 2.2 |
| Total | 182.5 | 182.5 | 182.5 | 132.5 | 132.5 | 132.5 |
| Yellowness | 1.50 | 1.54 | 1.58 | 1.23 | 1.51 | 1.80 |
| Glossiness | 85/76 | 73/32 | 83/75 | 77/68 | 79/70 | 71/57 |
| Hardness | D82 | D82 | D82 | D66 | D69 | D65 |

According to Examples in Table 1, it is found that the photocurable resin composition according to the embodiment of the present invention is a photocurable resin composition having a low yellowness and excellent transparency and glossiness when cured. Example 1 and Example 2 are different from each other in the component (C), but by using a compound having a molecular weight of 200 or less and having a hydroxyl group and a methacryloyl group as the component (C), a photocurable resin composition satisfying both required values of yellowness and glossiness at the time of curing is obtained. In addition, although the component (B) is different between Example 1 and Example 3, it is found that both of them give cured products having low yellowness and high glossiness, and the cured products have a sufficiently high hardness and satisfy the hardness required for the top coat layer.

According to Comparative Examples in Table 1, it is found that in Comparative Example 1, when a compound having a molecular weight of 200 or less and having a hydroxyl group but not having a methacryloyl group and having an acryloyl group is used as c'1, the glossiness of the cured product is low. In Comparative Examples 2 to 4, it is found that when compounds not satisfying a molecular weight of 200 or less are used as c'2 to c'4, the yellowness of the cured product is high, and the transparency is low. In Comparative Examples 5 to 7, it is found that when compounds not having hydroxyl groups are used as c'5 to c'7, the yellowness of the cured product is high, and the transparency is low.

Specifically, in Comparative Example 5, it is found that when a compound having a methacryloyl group but not satisfying a molecular weight of 200 or less and having no hydroxyl group is used as c'5, the yellowness of the cured product is high, and the transparency is low. In addition, in Comparative Example 6, when a compound not satisfying a molecular weight of 200 or less, not having a hydroxyl group or a methacryloyl group, and having an acryloyl group is used as c'6, it is found that not only the yellowness of the cured product is high and the transparency is low, but also the glossiness is insufficient. Furthermore, in Comparative Example 7, it is found that when a compound having a molecular weight of 200 or less and having a methacryloyl group but not having a hydroxyl group is used as c'7, the yellowness of the cured product is high, and the transparency is low.

As Comparative Examples 8 to 10, when a composition does not contain the component (B), the hardness of the cured product is low, and the cured product does not have hardness required for coating of a nail or an artificial nail.

INDUSTRIAL APPLICABILITY

The photocurable resin composition according to an embodiment of the present invention has hardness required for coating of a nail or an artificial nail, can form a cured product having excellent transparency and gloss, and thus can be widely used in the field of nail decoration.

This application is based on Japanese Patent Application No. 2020-124433, filed on Jul. 21, 2020, the disclosure content of which is hereby incorporated as its entirety by reference.

The invention claimed is:

1. A photocurable resin composition for a nail or an artificial nail, comprising components (A) to (D) below:

component (A): a urethane (meth)acrylate oligomer, component (B): trimethylolpropane tri (meth)acrylate, component (C): at least one selected from the group consisting of 2-hydroxypropyl methacrylate and 2-hydroxybutyl methacrylate, and component (D): a photoinitiator, wherein the composition comprises 40 to 60 parts by mass of the component (B), 15 to 30 parts by mass of the component (C), and 3 to 9 parts by mass of the component (D), relative to 100 parts by mass of the component (A), and a yellowness of a cured product of the photocurable resin composition for a nail or an artificial nail is 1.00 or less.

2. The photocurable resin composition for a nail or an artificial nail according to claim 1, wherein the component (A) comprises a urethane (meth)acrylate oligomer having a polyether skeleton.

3. The photocurable resin composition for a nail or an artificial nail according to claim 1, wherein the component (D) is an acylphosphine oxide-based photoinitiator and/or an alkylphenone-based photoinitiator.

4. The photocurable resin composition for a nail or an artificial nail according to claim 1, wherein a glossiness at 60° of the cured product of the photocurable resin composition for the nail or the artificial nail is 80 or more.

5. The photocurable resin composition for a nail or an artificial nail according to claim 1, used for a top coat.

6. A cured product of the photocurable resin composition for a nail or an artificial nail set forth in claim 1.

7. A method for coating a nail or an artificial nail, comprising: applying the photocurable resin composition for a nail or an artificial nail set forth in claim 1 on a nail or an artificial nail to form a coating film; and then irradiating the coating film with an active energy ray to cure the coating film.

8. The photocurable resin composition for a nail or an artificial nail according to claim 1, wherein glossiness at 20° of the cured product of the photocurable resin composition for the nail or the artificial nail is 70 or more.

* * * * *